United States Patent [19]
Whitney

[11] Patent Number: 5,603,731
[45] Date of Patent: Feb. 18, 1997

[54] METHOD AND APPARATUS FOR THWARTING THROMBOSIS

[76] Inventor: Douglass G. Whitney, 11200 Bowen Rd., Roswell, Ga. 30075

[21] Appl. No.: 553,011

[22] Filed: Nov. 3, 1995

Related U.S. Application Data

[63] Continuation of Ser. No. 342,717, Nov. 21, 1994, abandoned.

[51] Int. Cl.⁶ .......................... A61M 29/00; A61B 17/36
[52] U.S. Cl. .......................... 607/121; 607/122; 606/32; 606/33; 604/103; 604/104
[58] Field of Search .......................... 607/119–122, 126; 606/7, 32, 33, 41, 191, 195, 38; 604/20, 21, 96–99, 103, 104, 32, 33, 41; 623/1

[56] References Cited

U.S. PATENT DOCUMENTS

| | | | |
|---|---|---|---|
| 3,512,183 | 5/1970 | Sharp et al. | 3/1 |
| 3,723,754 | 3/1973 | Murayama et al. | 623/1 |
| 3,726,762 | 4/1973 | Puharich | 623/1 |
| 3,868,956 | 3/1975 | Alfidi et al. | 128/34 S |
| 4,188,927 | 2/1980 | Harris | 606/38 |
| 4,733,665 | 3/1988 | Palmaz | 606/191 |
| 4,776,337 | 10/1988 | Palmaz | 128/343 |
| 4,922,905 | 5/1990 | Strecker | 606/195 |
| 4,969,458 | 11/1990 | Wiktor | 606/194 |
| 5,019,090 | 5/1991 | Pinchuk | 606/194 |
| 5,078,736 | 1/1992 | Behl | 623/1 |
| 5,178,618 | 1/1993 | Kandarpa | 606/195 |
| 5,329,151 | 7/1994 | Anand et al. | 257/498 |
| 5,348,553 | 9/1994 | Whitney | 606/41 |

*Primary Examiner*—Angela D. Sykes
*Assistant Examiner*—Stephen Huang

[57] ABSTRACT

Thrombosis in a blood vessel is prevented in a patient's body by the steps of positioning an electrically conductive member in an expanded portion of the blood vessel, at a site where the body is exposed to blood platelets, and disposing an electronegative potential generator in or adjacent to the patient's body and connected to the conductive member for maintaining a negative bias on the conductive member. One form of generating the negative bias is by passing microwaves through the patient's body to contact an embedded diode which generates the negative potential. The current density is maintained at about 50 milliamps per square centimeter.

11 Claims, 2 Drawing Sheets

METHOD AND APPARATUS FOR THWARTING THROMBOSIS

This application is a continuation of Ser. No. 08/342,717 filed on Nov. 21, 1994, now abandoned.

BACKGROUND OF INVENTION

This invention relates generally to reducing thrombosis and more particularly to a method and apparatus for imposing an electronegative potential at a site where thrombosis is likely to be a problem to reduce platelet congregation.

It is common practice to repair the narrowed segment of a diseased blood vessel by radially expanding the affected area of the blood vessel using a balloon catheter, commonly called balloon angioplasty. Early failure of such vascular repairs can occur shortly after the application of balloon angioplasty (commonly within the first 24 hours after application) typically due to blood clots or obstruction caused by the deformed plaque at the narrowed portion of the blood vessel. Late failure of such repairs can occur (usually about 3–6 months after application of therapy) due primarily to constriction of the passage through the blood vessel due to overgrowth of the smooth muscle portion of the blood vessel wall. The percentage of early failures is typically low while the percentage of late failures to relatively high (estimated at 40–70%).

More recently, attempts to overcome these problems have employed the use of stents that are placed in the blood vessels and left after the balloon angioplasty is performed. Examples of such techniques and equipment used to perform this repair are shown in the following patents:

| U.S. Patent No. | Inventor | Issue Date |
| --- | --- | --- |
| 3,868,956 | Alfidi, et al. | 03/04/75 |
| 4,776,337 | Palmaz | 10/11/88 |
| 4,922,905 | Strecker | 05/08/90 |
| 4,969,458 | Wiktor | 11/13/90 |
| 5,019,090 | Pinchuk | 05/28/91 |

Experience has shown, however, that the stents have not been successful in overcoming the failures associated with balloon angioplasty. As a matter of fact, the stems have tended to fail more frequently than balloon angioplasty without the stents.

There have also been attempts to reduce blood clotting by using certain materials or circuits that generate an electronegative charge on the surface of artificial blood vessels used to surgically replace sections of the patient's vascular system or on the surface of receptacles to store blood. Examples of such techniques are illustrated in the following patents:

| U.S. Patent No. | Inventor | Issue Date |
| --- | --- | --- |
| 3,512,183 | Sharp, et al. | 05/19/70 |
| 3,723,754 | Murayama, et al. | 03/27/73 |
| 3,726,762 | Puharich, et al. | 04/10/73 |

This technology has not been applied to nonsurgical balloon angioplasty in which the original blood vessel is not removed. As a matter of fact, prior art U.S. Pat. No. 3,512,183 suggests that this technology is not applicable to living tissue in the blood vessel.

SUMMARY OF THE INVENTION

The invention disclosed herein is an improvement over my U.S. Pat. No. 5,348,553. In that patent, the expansion of the blood vessel was accomplished with a balloon catheter with an expandable stent expanded as an incident to the expansion of the blood vessel to physically keep the artery open and act as a conductor on which the electronegative potential is imposed. The electronegative charge was maintained through the stent on the interior surface of the blood vessel by extending a wire along the blood vessel from the stent to a device which maintained a sufficient electronegative potential on the stent to prevent the platelets from adhering to the vessel wall. It was necessary to carefully maintain the wire connection throughout the time that the offsetting electronegative potential was required. Because this connection passed along the blood vessel to a remote site and then through the blood vessel wall and the patient's skin to the exteriorly located electronegative potential generating device, the potential for infection and additional blood clot formation was created. The invention disclosed herein overcomes these and other problems and disadvantages by providing a technique for creating the electronegative potential on the stent without direct connection of the stent to an external potential source. As a result, the problems associated with the wire passing along the blood vessel and through the vessel wall and the patient's skin are eliminated. The invention utilizes an electronegative generator incorporated in the stem structure that is operated from externally of the patient without having to be physically connected to generator. The electronegative generator is disclosed as a microwave detector diode incorporated in the stent structure. The detector diode remains on the stent in the blood vessel and generates an electronegative potential on the stent when subjected to microwaves. Since the microwave will easily penetrate the body tissues of the patient, the electronegative potential can be easily generated from outside the patient is a noninvasive manner. The amount of potential imposed on the stent can be controlled by a voltage limiting array.

These and other features and advantages of the invention will become more clearly understood upon consideration of the following detailed description and accompanying drawings wherein like characters of reference designate corresponding parts throughout the several views and in which:

These features and the following detailed description disclose specific embodiments of the invention; however, it is to be understood that the inventive concept is not limited thereto since it may be embodied in other forms.

DETAILED DESCRIPTION OF ILLUSTRATIVE EMBODIMENTS

Figure 1:
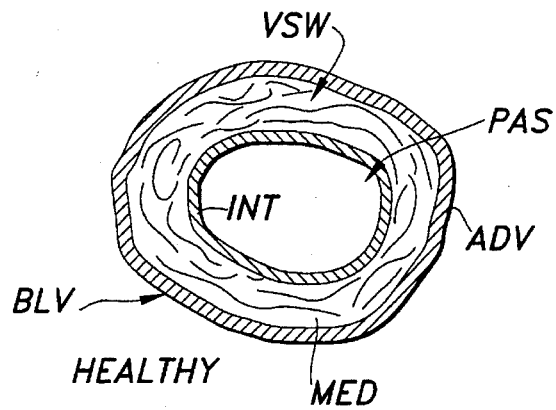
FIG. 1 is an enlarged cross-sectional view of a healthy blood vessel.

The vessel wall VSW of a normal artery or other blood vessel BLV has several portions when seen in cross-section. There is an outer layer or adventicia ADV on its exterior surface, a central portion or media MED, and a surface lining of cells or intima ITM on its luminal or interior surface. As schematically illustrated in FIG. 1, the interior and exterior surfaces INT and EXT of the blood vessel BLV are oppositely charged with an electronegative charge on the interior surface INT and an electropositive charge on the exterior surface EXT. Thus, the negative charge on the interior surface INT serves to repel the negatively charged blood passing through the blood vessel and maintain free passage of the blood. In the event of an injury to the vessel wall, these charges reverse so that the negatively charged platelets in the blood stream are attracted to the interior surface INT to start the blood clotting and injury healing process. This reversal of charge is called a current of injury. This electropositive current of injury is responsible, to a great extent, for the normal response of the body to control hemorrhage or bleeding from an injured vessel wall.

Figure 2:
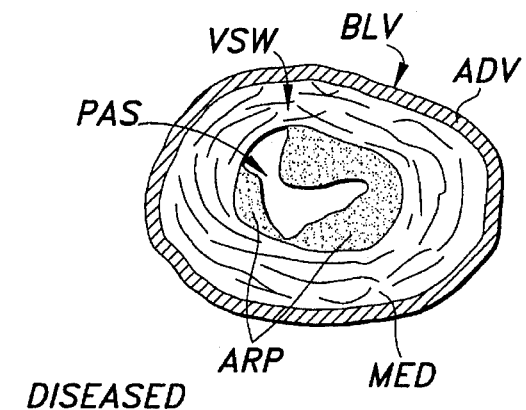
FIG. 2 is an enlarged cross-sectional view of a diseased blood vessel.

Whereas a normal artery or other blood vessel has an intimal cell lining on its luminal or interior surface, a diseased artery is frequently denuded of this intimal lining and has a raw surface of arteriosclerotic plaque ARP as seen in FIG. 2. The normal electronegative surface potential of the healthy intimal lining may not be present. The process of balloon angioplasty, in fact, injures an artery or vessel wall and sets the stage for recurrence of injury which can, in fact, be responsible for failure of the balloon angioplasty.

Figure 3:
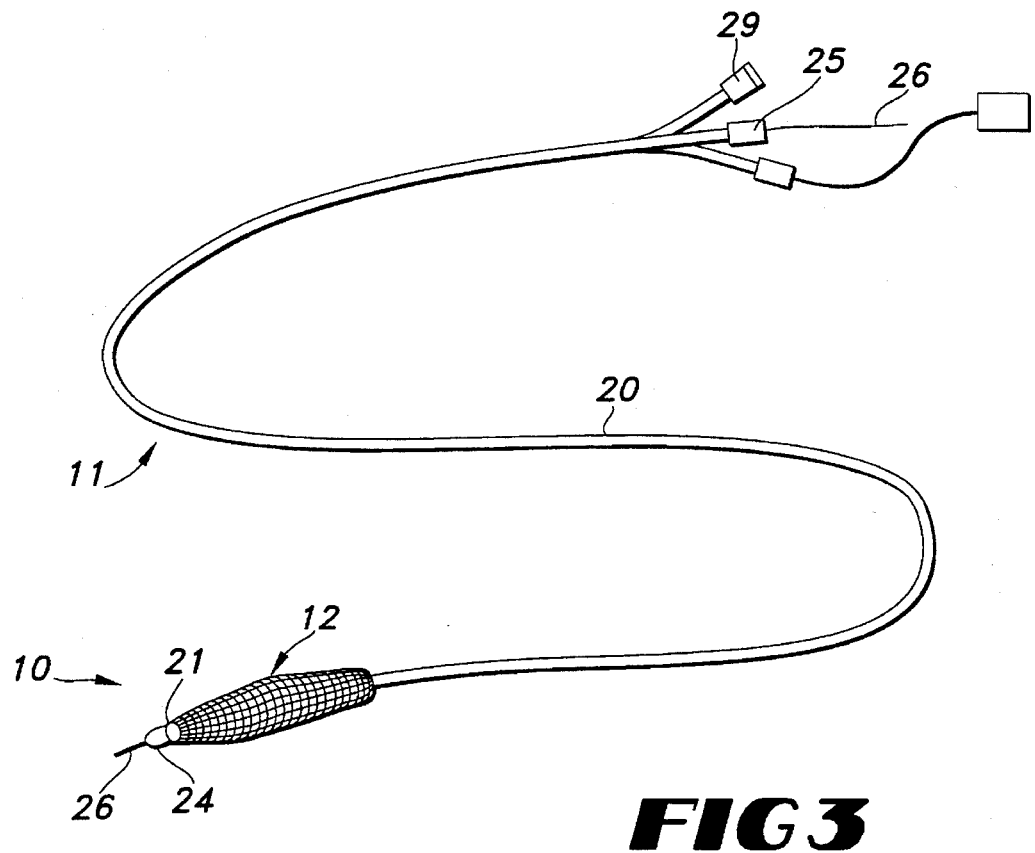
FIG. 3 is a view illustrating the system of the invention.

Referring to FIG. 3, the apparatus of the invention is a system 10 which includes a balloon catheter 11 on which is carried an electrically conductive stent structure 12. The catheter 11 corresponds generally to a balloon catheters used for balloon angioplasty and includes a multi-lumen elongated thin main body 20 on the leading end of which is mounted an inflatable balloon 21. The body 20 defines a guide wire lumen therethrough from its leading end 24 to the wire inserting fitting 25 at its opposite end to fit over the guide wire 26 normally associated with the insertion of the catheter 11 into the patient's blood vessel. The body 20 also defines a pressure lumen therein which communicates with the balloon 21 on the leading end of the catheter and opens through the pressure fitting 29 at the opposite end of the body 20 as is typical with balloon catheters.

The stent structure 12 may have any of a wide variety of constructions as long as it is capable of carrying the electronegative potential within the range required to offset the current of injury in the blood vessel and is also capable of being located on the interior surface INT of the patient's blood vessel. Preferably, the stent structure 12 is capable of being nonelastically expanded from a diameter smaller than the free passage through that portion of the blood vessel which has been narrowed to the accumulated arteriosclerotic plaque. The stent structure 12 illustrated in FIG. 4 has an open plastic or metal wire mesh construction which is electrically conductive. Any of a wide variety of materials may be used without departing from the scope of the invention. Preferably, the metal wire mesh is in an annealed condition so that the stent can be expanded by the balloon 21 into contact with and supports the blood vessel wall and will have limited recovery to remain in contact with the vessel wall after the balloon 21 has been deflated.

Figure 4:
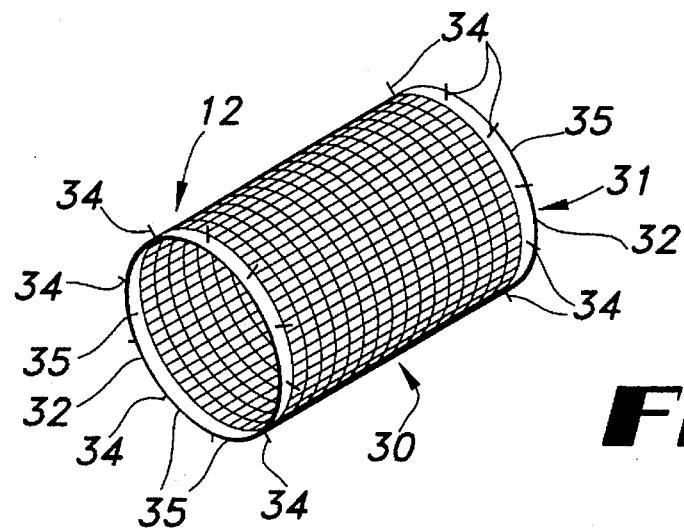
FIG. 4 is an enlarged perspective view of the stent used in the invention.

As seen in FIG. 4, the stent structure 12 includes a central section 30 and a pair of end sections 31 at opposite ends of the central section 30. At least the interior surface of the central section 30 is uninsulated so that any electrical potential imposed on the central section 30 will be imposed on this interior surface.

Each of the end sections 31 includes a circular portion 32 coaxially arranged with respect to the central section 30 and nonelastically expandable along the central section 30 as the stent structure 12 is expanded by the balloon catheter 11. The circular portion 32 is also electrically conductive but is insulated so that the electrical potential imposed thereon is isolated from the surface of the portion 32. Each of the end sections 31 also includes a plurality of outwardly projecting prongs 34 connected to the circular portion 32 and projecting outwardly therefrom generally radially of the central axis of the stent structure 12. The prongs 34 are also electrically conductive but insulated expect for their projecting tips so that any electrical potential imposed on the circular portion 32 will be exposed at the tips.

Figure 5:
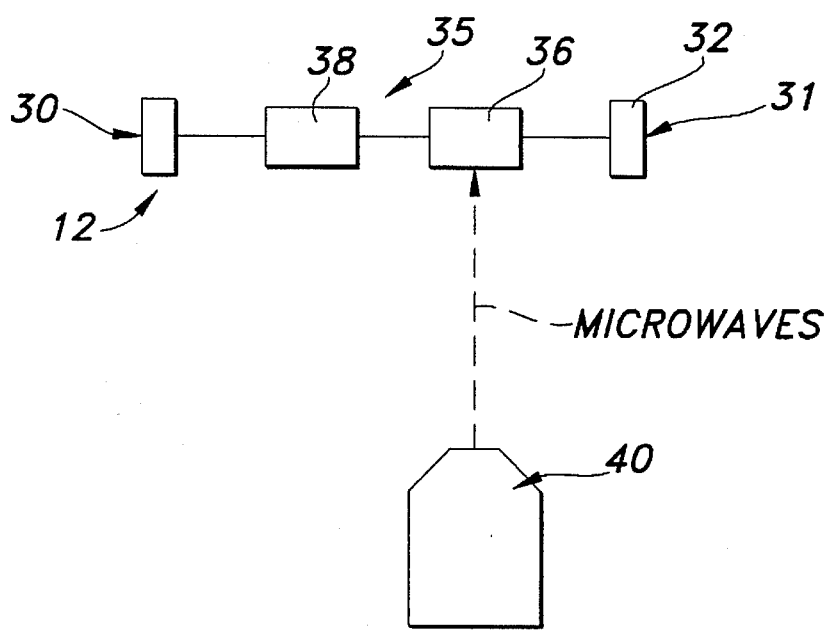
FIG. 5 is an electrical schematic illustrating the operation of the invention.

One or more electronegative potential generators 35 electrically and physically interconnect the central section 30 of the stent structure 12 with the end sections 31. As seen schematically in FIG. 5, each of the generators 35 includes a microwave detector diode 36 which generates an electrical potential thereacross in response to microwaves being imposed thereon. The particular diode 36 is selected to produce a voltage thereacross sufficient to offset the current of injury potential that the body tries to impose 30 on the surface INT of the blood vessel wall after the balloon angioplasty is performed. To limit the voltage that the diode 36 may generate thereacross, a zener diode array 38 may be used to connect the diode 36 to the central section 31 of the stent structure 12. Both the diode 36 and the array 38 are microscopic in size so as not to interfere with the installation of the stent structure 12 nor the blood flow of the patient once installed. Moreover, the stent structure 12 is made out of material that is biocompatible. The diode 36 is connected to the central section 30 of the stent structure 12 so as to impose an electronegative potential thereon and connected to the end sections 31 so as to impose the corresponding electropositive voltage thereon. Because the end sections 31 are insulated, however, this voltage will only be exposed to the patient's body through the projecting tips of the prongs 34. As will become more apparent, the projecting tips of the prongs 34 will be embedded in the blood vessel wall and thus isolated from the blood passing through the blood vessel.

Initially, the reduced diameter stent structure 12 is mounted over the collapsed balloon 21 on the catheter 11 so that it will remain in place over the balloon as it is placed in position in the diseased area of the blood vessel. As the balloon 21 is expanded into position in the blood vessel, it also expands the stent structure 12 as an incident to the expansion of the blood vessel. Because the stent structure is non-elastically expanded (i.e., it remains expanded after it is expanded), the stent structure 12 does not collapse as the balloon 21 is collapsed and thus remains in position. This serves to help keep the blood vessel open while at the same time causing the prongs 34 to penetrate the blood vessel wall BLV. AS a result, the tips of the prongs 34 will impose the electropositive potential inside the blood vessel wall and the prongs 34 will help keep the stent structure 12 in position in the blood vessel. After the balloon 21 is collapsed, the balloon catheter 11 is then withdrawn from the patient.

To maintain the electronegative potential on the central section 30 of the stent structure 12, a microwave generator 40 is used to excite the detector diode 36 as soon as the stent structure 12 is expanded. This insures that the current of injury positive potential will be offset by the electronegative potential on the central section 30 of the stent structure 12 and thus prevents the platelets in the blood from being attacked to the site as soon as the balloon 21 is collapsed. It is anticipated that the microwave generator 40 will be strapped to the outside of the patient over the site of the stent structure 12 as long as the electronegative potential is needed at the site. The zener diode array 38 serves to limit the electronegative potential imposed on the central section 30 in the event the patient is inadvertently exposed to additional microwaves.

The stent structure 12 remains in place in the blood vessel after the procedure. Therefore, the structure 12 is made of a material which is biocompatible.

It will be appreciated that the invention is not limited to the application in balloon angioplasty an can be used at a site where thrombosis is likely to be a problem and where the electronegative potential will reduce blood platelet congregation. As a result, the initial phase of clot formation is prevented and allows incisions to be closed without the problem of thrombosis occurring. Applications include long time indwelling catheters, artificial grafts, heart valve replacements, and orthopedic implants. Where an implanted metal device is used, the electronegative generators 36 can be applied directly to the implanted device while a biocompatible compliant substrate or covering that will carry the generated electronegative charge can be used in other applications not utilizing an implanted metal device. Where a covering is used, it should permit the covered site to heal while the covering remains in place.

I claim:

1. A method of preventing thrombosis at a site, in a patient's body exposed to platelets, on which site the body has imposed an electropositive current of injury charge, said method comprising the steps of:
   (a) positioning within said patient's body an electrically conductive member having first and second portions insulated from each other, and a remotely actuatable electrical potential generator capable of producing an electropositive potential and an electronegative potential, said potential generator being electrically coupled to said conductive member to induce, when activated, an electronegative potential on said first portion of said conductive member and an electropositive potential on said second portion of said conductive member;
   (b) electrically connecting said second portion of said conductive member to said patient's body and exposing said first portion of said conductive member to said site and to said platelets;
   (c) imposing an actuation signal through said patient's body and onto said electrical potential generator for activating said generator to produce an electropositive potential and an electronegative potential, said electronegative potential being sufficient to offset the electropositive current of injury imposed on the site by the patient's body;
   (d) said activation signal being predetermined to maintain a current density of about 50 milliamps per square centimeter on said first portion of said conductive member.

2. A method of preventing thrombosis in a patient's body exposed to blood platelets by expanding the narrowed portion of a blood vessel in the patient, said blood vessel having an interior surface, comprising the steps of:
   (a) positioning an electrically conductive member with a microscopic electronegative potential generator connected thereto so that said conductive member substantially covers a portion of said interior surface, said generator being constructed and arranged to cause an electrical potential to be generated thereacross in response to an activation signal generated remotely of but imposed on said electronegative potential generator;
   (b) after said conductive member is substantially covering said portion of said interior surface, imposing said activation signal on said electronegative potential generator through the patient's body to cause said electronegative generator to maintain an electronegative potential on said conductive member sufficient to thwart blood platelet congregation around said conductive member; and
   (c) said conductive member being a stent capable of being nonelastically expanded and wherein step (a) comprises the substeps of:
      (a1) locating said stent over a collapsed balloon of a balloon catheter where the stent has an initial diameter smaller than the narrowed portion of the blood vessel;
      (a2) inserting the balloon catheter into the narrowed portion of the blood vessel until the collapsed balloon on the catheter is in registration with the narrowed portion of the blood vessel while holding the stent in position over the collapsed balloon of the catheter; and
      (a3) inflating the collapsed balloon to forcibly enlarge the narrowed portion of the blood vessel and nonelastically enlarge the stent into contact with the narrowed portion of the blood vessel;
wherein the step (b) further includes:
   (b1) imposing said activation signal on said electronegative generator to maintain an electronegative potential on the stent at least to offset the current of injury potential generated as a result of expanding the blood vessel; and
   (b2) imposing microwaves on said microwave detector diode so as to maintain a current density of about 50 milliamps per square centimeter on the interior surface of the blood vessel.

3. A system for thwarting blood platelet congregation at an injured site in a patient's body wherein said body generates a current of injury charge to electrically attract blood platelets to said site, said system comprising:
   (a) an electrically conductive member disposed in said patient's body adjacent to said injured site for holding said injured site in a healing position;
   (b) a microscopic electronegative potential generator disposed within the body of said patient and electrically connected to said conductive member, said generator being adapted to impose an electronegative potential on said conductive member, said microscopic electronegative potential generator being adapted to receive activation signals while embedded in said patient's body, and means for generating an activation signal through said patient's body for causing said electronegative potential generator to be actuated to impose a sufficient electronegative potential on said conductive member to thwart blood platelet congregation at said injured site;
   (c) said generator also generating an electropositive potential delivered to said body;
   (d) said site being a blood vessel having an interior through which blood passes and wherein said electrically conducting member is an expandable stent disposed in expanded condition against the interior of said blood vessel holding said blood vessel in an expanded condition, said stent having portions insulated from each other and to which said electropositive potential and said electronegative potential are respectively fed;
   (e) said insulated portions of said stent including a central portion coupled to receive said electronegative potential and end portion coupled to receive said electropositive potential;

(f) said end portion having outwardly protruding electrically conductive prongs.

4. A method of preventing thrombosis at a site in a patient's body exposed to platelets, on which site the body has imposed an electropositive current of injury charge, said method comprising the steps of:

(a) positioning within said patient's body an electrically conductive member and an electronegative potential generator, electrically connected to said conductive member, said conductive member having a first portion and a second portion insulated from each other;

(b) electrically connecting said positive portion to said patient's body and exposing said negative portion to said site and to said platelets;

(c) imposing an actuation signal through said patient's body and onto said electronegative potential generator for activating said electronegative generator to produce an electropositive charge and an electronegative charge;

(d) imposing said electropositive charge on said first portion and said electronegative charge on said second portion sufficient that the charge on said second portion sufficiently will offset the electropositive current of injury charge imposed on said site;

(e) said electrically conductive member comprising a tubular stent having a central portion and an end portion and wherein said first portion is said central portion and said second portion is said end portion of said stent; and (f) prongs protruding outwardly from said conductive member.

5. A thrombosis thwarting stent for buttressing an injured section of an artery of a patient and preventing congregation of blood platelets at the injured section of the artery, the artery having an artery wall, said stent comprising:

a substantially tubular electrically conductive body sized to be received within and bear against the artery for buttressing the artery against collapse;

a remotely actuatable electrical potential generator for generating an electronegative charge and an electropositive charge, said generator being incorporated into said tubular body so as not to restrict flow of blood through the artery when the tubular body is positioned therein;

first coupling means for coupling said generator to said conductive body to impart, upon activation of said generator, an electronegative charge to said conductive body; and second coupling means for coupling said generator to a selected location of the artery wall to impart, upon activation of said generator, an electropositive charge to the artery wall.

6. A stent as claimed in claim 5 and wherein said second coupling means comprises at least one prong projecting radially from said conductive body and electrically insulated therefrom, said prong being sized to extend into the artery wall when the stent is in place within the artery.

7. A stent as claimed in claim 6 and wherein said conductive body comprises a central portion and an end portion electrically insulated from each other and wherein said at least one prong projects radially from said end portion.

8. A stent as claimed in claim 5 and wherein said electrical potential generator comprises a microwave detector diode that generates an electrical potential thereacross in response to microwaves being imposed thereon.

9. A stent as claimed in claim 8 and further comprising means for limiting the electrical potential generated by said microwave detector diode to a predetermined maximum potential.

10. A stent as claimed in claim 9 and wherein said means for limiting comprises a zener diode array connected in series with said microwave detector diode.

11. A stent as claimed in claim 8 and further comprising means outside the patient's body for generating microwaves and imposing the microwaves through the patient's body and on said microwave detector diode to activate said diode to produce an electrical potential.

* * * * *